US009439871B2

(12) United States Patent
Kim et al.

(10) Patent No.: US 9,439,871 B2
(45) Date of Patent: Sep. 13, 2016

(54) METHOD FOR PREPARING NANO PARTICLES

(71) Applicants: Kab Sig Kim, Seoul (KR); Joo Won Park, Seoul (KR)

(72) Inventors: Kab Sig Kim, Seoul (KR); Joo Won Park, Seoul (KR)

(73) Assignee: BIO-SYNECTICS, INC., Seoul (KR)

( * ) Notice: Subject to any disclaimer, the term of this patent is extended or adjusted under 35 U.S.C. 154(b) by 70 days.

(21) Appl. No.: 14/344,256

(22) PCT Filed: Sep. 21, 2012

(86) PCT No.: PCT/KR2012/007581
§ 371 (c)(1),
(2) Date: Mar. 11, 2014

(87) PCT Pub. No.: WO2013/042978
PCT Pub. Date: Mar. 28, 2013

(65) Prior Publication Data
US 2015/0031707 A1    Jan. 29, 2015

(30) Foreign Application Priority Data
Sep. 21, 2011   (KR) .......................... 10-2011-0095075

(51) Int. Cl.
| | |
|---|---|
| *A61K 9/14* | (2006.01) |
| *A61K 9/50* | (2006.01) |
| *A61K 38/00* | (2006.01) |
| *A61K 38/17* | (2006.01) |
| *A61K 38/45* | (2006.01) |
| *A61K 9/51* | (2006.01) |
| *A61K 31/496* | (2006.01) |
| *A61K 31/122* | (2006.01) |
| *A61K 31/443* | (2006.01) |

(52) U.S. Cl.
CPC ............. *A61K 9/5192* (2013.01); *A61K 9/145* (2013.01); *A61K 9/146* (2013.01); *A61K 9/5123* (2013.01); *A61K 9/5138* (2013.01); *A61K 9/5146* (2013.01); *A61K 31/122* (2013.01); *A61K 31/443* (2013.01); *A61K 31/496* (2013.01)

(58) Field of Classification Search
None
See application file for complete search history.

(56) References Cited

U.S. PATENT DOCUMENTS

| | | | |
|---|---|---|---|
| 5,145,684 A | 9/1992 | Liversidge et al. | 424/489 |
| 5,202,129 A | 4/1993 | Samejima et al. | 424/489 |
| 5,302,401 A | 4/1994 | Liversidge et al. | 424/501 |
| 5,534,270 A | 7/1996 | De Castro | 424/490 |
| 6,592,903 B2 | 7/2003 | Ryde et al. | 424/489 |
| 8,226,983 B2 | 7/2012 | Hirokawa et al. | 424/489 |
| 8,333,990 B2 | 12/2012 | Rosenberg et al. | 424/455 |
| 2002/0168402 A1 | 11/2002 | Kipp et al. | 424/450 |
| 2003/0104068 A1 | 6/2003 | Mathiowitz et al. | 424/491 |
| 2003/0185869 A1 | 10/2003 | Wertz | 424/405 |
| 2004/0067251 A1 | 4/2004 | Johnston et al. | 424/465 |
| 2006/0193920 A1 | 8/2006 | Bosch et al. | 424/489 |
| 2007/0248675 A1 | 10/2007 | Tae et al. | 424/486 |
| 2008/0113025 A1* | 5/2008 | Devane et al. | 424/470 |
| 2009/0202646 A1 | 8/2009 | Kim et al. | 424/489 |
| 2010/0172993 A1 | 7/2010 | Singh et al. | 424/489 |
| 2013/0005643 A1 | 1/2013 | Kim et al. | 514/1.1 |

FOREIGN PATENT DOCUMENTS

| | | | | |
|---|---|---|---|---|
| CN | | 1668281 | 9/2005 | ............... A61K 9/14 |
| CN | | 101365449 | 2/2009 | ......... A61K 31/4535 |
| CN | | 101484170 | 7/2009 | ........... A61K 31/485 |
| KR | 10-2007-0107841 | | 11/2007 | ............... B82B 3/00 |
| KR | 10-2007-0114294 | | 11/2007 | ........... A61K 31/513 |
| KR | 10-2008-0017161 | | 2/2008 | ............. A61K 47/36 |
| KR | 10-2009-0041426 | | 4/2009 | ............... A61K 9/14 |
| KR | 10-2011-0106247 | | 9/2011 | ............... A61K 9/16 |
| WO | WO 2004/041250 | | 5/2004 | ............... A61K 9/14 |
| WO | WO 2006/060698 | | 6/2006 | ......... A61K 31/4535 |
| WO | WO 2007/150074 | | 12/2007 | ........... A61K 31/485 |
| WO | | 2008/126797 | 10/2008 | ............... A61K 9/14 |

OTHER PUBLICATIONS

He et al.; AAPS PharmSciTech, vol. 12, No. 1, Mar. 2011.*
BASF Technical Information Bulletin dated Apr. 2010.*
Will, Scott; Grain&Feed Milling Technology; Mar./Apr. 2010; pp. 18-19.*
Mochalin, V., et al., Manufacturing Nanosized Fenofibrate by Salt Assisted Milling, Pharmaceutical Research, vol. 26, No. 6, Jun. 2009.
Wongmekiat, A., et al., "Preparation of Drug Nanoparticles by C0grinding with Cyclodextrin: Formation Mechanism and Factors Affecting Nanoparticle Formation", Chem. Pharm. Bull. 55(3), 359-363 (2007).
The Theory and Practice of Industrial Pharmacy, Chapter 2, "Milling", p. 45, (1986).
International Search Report (ISR) in PCT/KR2012/007581 dated Feb. 7, 2013.
Extended European Search Report dated May 22, 2015, issued in European Application No. 12834544.4.

* cited by examiner

*Primary Examiner* — Jeffrey T Palenik
(74) *Attorney, Agent, or Firm* — Harness, Dickey & Pierce, P.L.C.

(57) ABSTRACT

The present invention relates to a method for manufacturing nano-scale particles of an active material. More particularly, the present invention relates to a method which uniformly mixes a surfactant having an HLB value of 8 or more and a melting point or glass transition temperature of 80° C. or lower and an active material, and mills the mixture using a roller mill, to thereby prepare nanoparticle powder from the active material.

14 Claims, No Drawings

METHOD FOR PREPARING NANO PARTICLES

CROSS-REFERENCE TO RELATED APPLICATIONS

This application is a national phase application of PCT Application No. PCT/KR2012/007581, filed on Sep. 21, 2012, which claims the benefit and priority to Korean Patent Application No. 10-2011-0095075, filed Sep. 21, 2011. The entire disclosures of the applications identified in this paragraph are incorporated herein by references.

TECHNICAL FIELD

The present invention relates to a method for preparing nanoscale particles of an active ingredient. More specifically, the present invention relates to a method for preparing nanoparticle powder of an active ingredient by uniformly mixing an active ingredient with a surfactant having an HLB value of 8 or more and a melting point or a glass transition temperature of 80° C. or lower; and grinding the mixture by using a roller mill.

BACKGROUND

In various industrial fields, there has been a constant demand for a technique of an effective and rapid preparation of very fine particles in regular size. Such fine particles in regular size have many advantages. Among them, good flowability and little deviation in particle interaction are especially very advantageous in industrial applications. For example, in the drug industry, the particle size of a therapeutic agent greatly affects the dissolution rate, bioavailability, formulation and the like, and as deviation in the interaction between the particles of a therapeutic agent becomes smaller, the overall stability of the therapeutic agent improves.

In medicinal products, if the particle of a therapeutic agent is made into nanoscale size, the following advantages are obtained. First of all, for drugs having a small enteral absorption rate in oral administration, more absorption can be achieved and thus the bioavailability of the therapeutic agent can be increased, as compared with those of a bigger size. Furthermore, the dosage form of drugs can vary. For instance, a drug that has been administered only via oral route may be administered by inhalation. In a controlled-release drug formulation, the release rate of a therapeutic agent is a very important factor. When the particle size of the therapeutic agent is formed in nanoscale, the particle size becomes relatively more uniform, thus the release rate can become more expectable, allowing the provision of more effective therapeutic agent.

In order to capitalize on the advantages of uniform nanoparticles as described above, many attempts have been made to prepare an active ingredient as a nanoparticle. For this object, mechanical techniques such as crushing, grinding, milling and the like have been conventionally employed to make relatively large particles smaller. Recently in the pharmaceutical industry, a method using an air-jet mill for milling a large amount of drugs to a size range suitable for medicinal or pharmaceutical use has been commonly used. However, according to U.S. Pat. No. 5,534,270 and Lachman, et al. [The Theory and Practice of Industrial Pharmacy, Chapter 2, "Milling," p. 45, (1986)], such conventional mechanical processes have been generally recognized as having a limitation of possible minimum particle size of about tens of micrometers.

It has been reported that nanoscale fenofibrate was obtained by a method comprising mixing fenofibrate and sodium chloride (weight ratio of 1:7) using a ball mill and dry-grinding the mixture using an attritor mill [Vandym N. Mocahlin et al., Pharmaceutical Research, Vol. 26, No. 6, 1365~1370, June 2009], wherein sodium chloride is a very hard material and when it is ground by a ball mill, it serves as a grind media and at the same time prevents re-coagulation of the ground fenofibrate.

Keiji Yamamoto et al. asserted that nanoparticles of drug may be prepared by grinding the drug along with cyclodextrin using a rod mill [Chem. Pharm. Bull. 55(3), 359-363 (2007)]. They asserted that the amount of cyclodextrin used in this method is about twice the active ingredient in molar ratio—i.e., about four times in weight ratio, and that humidity for hydrating all used cyclodextrin is needed and it is disadvantageous if the humidity is too high or too low.

Furthermore, in WO 2008/126797, Hirokawa, Takashi et al. disclose a process for providing a nanoscale active ingredient by mixing sodium chloride and polyol compound with an active ingredient and then subjecting it to a wet-milling process without the use of grinding media. However, these processes use excessive sodium chloride and polyol compound, and thus essentially require a step for removing sodium chloride and polyol compound in order to use the obtained nanoparticles in medicinal products.

U.S. Pat. No. 5,202,129 discloses a method for preparing fine particles of a poorly water-soluble drug by mixing the drug with 2.5 times or more of low-molecular weight saccharide or sugar alcohol and then dry-grinding the mixture. However, this method has a problem in that because a large amount of saccharide is used, for actual use in medicinal products, it is necessary to remove the saccharide by dispersing the ground mixture in water, filtering the dispersed mixture and drying the filtered mixture.

U.S. Pat. No. 5,145,684 discloses a method for preparing particles of a poorly water-soluble drug in a size of hundreds of nanometers by wet-milling the poorly water-soluble drug in the presence of a non-crosslinked polymer. This technique should be applied after preparing the drug in a particle size of 100 micrometers or less by using a conventional milling process. In this method, the time for preparing particles within the target size range depends on the mechanical device used therefor. When a ball mill is used, 5 days or longer is required. However, when a high shear media mill is used, the particles can be prepared within 1 day. However, since the nanoparticles obtained in this method are in liquid phase, in order to make them in powder type, a process of spray dry or freeze dry should be conducted. During the drying process, however, coagulation of particles occurs and when the obtained powder is re-dispersed in liquid, it is difficult to obtain a dispersion of particles in nanometer scale. In order to solve such a problem, U.S. Pat. No. 5,302,401 discloses an anti-coagulation agent employed during lyophilization. Additionally, U.S. Pat. No. 6,592,903 B2 discloses use of a stabilizer, a surfactant and an anti-coagulation agent during a spray-dry process. Furthermore, US Patent Application Publication No. 2003/0185869 A1 discloses an application of a wet milling technique using lysozyme as a surface stabilizer to some poorly soluble drugs. However, in this case, since the surface stabilizer is a protein, there are many restrictions in drying and accordingly only the preparation in liquid phase is disclosed.

US Patent Application Publication No. 2002/0168402 discloses a method for preparing nanoparticles using piston gap homogenization. However, in order to use piston gap homogenization, a pretreatment process using jet mill or hammer mill for grinding particles into uniform size is required. In addition, because this process is not suitable for highly viscous solutions, it should be performed in a state where the concentration of active gradient is low.

As another conventional method, there is a recrystallization technique which provides fine particles of an active ingredient by changing the environment of a solution containing the active ingredient dissolved therein to cause the precipitation or crystallization of the solute. The recrystallization technique can be carried out in two different ways: one being comprised of dissolving a therapeutic agent in a suitable solvent and lowering the temperature, thereby changing the solubility of the therapeutic agent to precipitate particles; and the other being comprised of adding an antisolvent to a solution containing the therapeutic agent dissolved therein, thereby decreasing the dissolving ability of the solvent to precipitate particles. However, most such recrystallization techniques usually require use of an organic solvent harmful to humans, and flocculation or coagulation of the particles in a wet condition occurs during a drying process after filtration of the precipitated particles. As a result, the final particles may not be uniform in size.

US Patent Application Publication No. 2003/0104068 A1 discloses a method for preparing fine particles by dissolving a polymer in an organic solvent, dissolving or dispersing a protein drug therein, rapidly cooling the solution to ultra-low temperature for solidification, and lyophilizing the product to provide fine powder. In this case, however, the protein drug may be denatured by the contact with an organic solvent, and the process needs the rapid cooling and lyophilizing processes, and thus is not economical.

In addition, there are techniques of reducing particle size by using emulsification. Such emulsifying methods are commonly used in the cosmetic field, and provide fine particles by melting poorly water-soluble substances by heat or dissolving them in an organic solvent, and adding the melted or dissolved substances to an aqueous solution containing a surfactant dissolved therein, with stirring at high speed or with sonication to disperse the added substances. However, in this case, a step for removing water is required to provide fine particles in powder form, and many restrictions are generated during the water-removal step. Furthermore, when an organic solvent is used to dissolve the poorly water-soluble substance, there always is a concern that the residual organic solvent will be harmful to humans.

US Patent Application Publication No. 2004/0067251 A1 discloses a method for preparing fine particles by dissolving an active ingredient in an organic solvent and spraying the resulting solution into an aqueous solution containing a surfactant dissolved therein. This method uses an organic solvent, and since the prepared particles exist in an aqueous phase, a drying process is required for removing water used as solvent, to render the particles in powder form. During the drying process, however, coagulation of the particles occurs and thus it is hard to re-disperse them in nanoscale size.

DETAILED DESCRIPTION

Technical Purpose

The present invention seeks to solve the above-mentioned problems of the prior arts. In particular, the present invention can overcome the limitation of difficulty in preparing particles having a size smaller than micrometer-scale in a traditional dry grinding process, and can solve the problem of particle growth and size-up during the water-removal step after the grinding step due to the use of a lot of water in a traditional wet grinding process. In addition, the present invention seeks to provide a method for preparing nanoparticles easily and effectively, even in the case of active ingredients having relatively low water solubility.

Technical Means

Accordingly, the present invention provides a method for preparing nanoparticle powder of an active ingredient, comprising: (1) uniformly mixing an active ingredient with a surfactant having an HLB value of 8 or more and a melting point or a glass transition temperature of 80° C. or lower; and (2) grinding the mixture obtained in step (1) by using a roller mill.

The mixture obtained in step (1) may further comprise a biocompatible polymer, if necessary.

In addition, the mixture obtained in step (1) may further comprise a saccharide or a salt, if necessary.

According to an embodiment of the present invention, the method for preparing nanoparticle powder of an active ingredient of the present invention can be performed preferably, for example, through the following steps:

1) uniformly mixing an active ingredient, a surfactant having an HLB value of 8 or more and a melting point or a glass transition temperature of 80° C. or lower, optionally a biocompatible polymer, and optionally a saccharide or a salt; and 2) continuously grinding the mixture obtained in step 1) by using a roller mill.

According to another embodiment of the present invention, the method for preparing nanoparticle powder of an active ingredient of the present invention can be performed preferably, for example, through the following steps:

1) mixing an active ingredient, a surfactant having an HLB value of 8 or more and a melting point or a glass transition temperature of 80° C. or lower, and optionally a biocompatible polymer;

2) optionally adding a saccharide or a salt to the mixture obtained in step 1) and uniformly mixing the resulting mixture; and 3) continuously grinding the mixture obtained in step 2) by using a roller mill.

In the present invention, the active ingredient is a material that exhibits physiological activity in, for example, medicinal products, functional foods, cosmetics and the like. Preferably, the active ingredient is one or more selected from the group consisting of physiologically active organic compounds, organometallic compounds, natural extracts, peptides, proteins and polysaccharides. There is no special limitation to its state at room temperature such as solid phase or liquid phase, or to its electrical form such as neutral or ionic form.

The term "nanoparticle(s)" used herein refers to a particle(s) wherein 90% or more of the particles have an average particle size of 5 μm or less, preferably 2 μm or less, more preferably 1 μm or less, still more preferably 0.5 μm or less.

The method for preparing nanoparticles of the present invention essentially uses a surfactant having an HLB value of 8 or more and a melting point or a glass transition temperature of 80° C. or lower. If the HLB value of the essential surfactant is less than 8, nanoparticles having good water dispersability cannot be prepared. If its melting point or glass transition temperature is higher than 80° C., the grinding of the active ingredient cannot be performed well. In the present invention, by essentially using a surfactant satisfying the above requirements, the uniform mixing with the active ingredient and optionally a biocompatible polymer can be achieved, and as a result nanoparticles with more uniform particle size distribution can be obtained.

In the present invention, concrete examples of the essential surfactant having an HLB value of 8 or more and a melting point or a glass transition temperature of 80° C. or lower include, but are not limited to, phospholipids, benzalkonium chloride, glycerin esters of fatty acid, cetomacrogol, polyoxyethylene alkyl ethers, polyoxyethylene stearate, polyoxyethylene fatty acid esters, sorbitan esters, polyoxyethylene castor oil derivatives, polyoxyethylene sorbitan fatty acid esters, sucrose fatty acid esters, PEG-cholesterol, PEG-vitamin E and mixtures thereof. In the present invention, a surfactant other than the above essential surfactant can be used together as an auxiliary surfactant.

The biocompatible polymer useful in the present invention may be that used in medicinal products, foods and cosmetics, and there is no limitation to the electrical form—such as ionic or nonionic. Those having a melting point of 40° C. or higher are preferable for maintenance of long-term particle stability of the drug in the prepared powder, and those having a glass transition temperature of 200° C. or lower are suitable for grinding heat-sensitive materials with low grinding energy. Concrete examples of the biocompatible polymer useful in the present invention include, but are not limited to, gelatin, casein, dextran, gum arabic, tragacanth, polyethyleneglycols, carboxymethylcellulose, hydroxypropylcellulose, hydroxypropylmethylcellulose, methylcellulose, hydroxyethylcellulose, hydroxypropylmethylcellulose phthalate, noncrystalline cellulose, polyvinylalcohol, polyvinylpyrrolidone, poloxamers, Eudragit®, lysozyme, albumin and the like. Each of the above examples may be used alone or in combination with other(s), and may be mixed with the essential surfactant.

The saccharide useful in the present invention is of a concept including monosaccharide compounds, disaccharide compounds, polysaccharide compounds and sugar alcohols, particularly including glucose, lactose, mannitol, sucrose, xylitol, chitosan, starch, fiber, a mixture thereof and the like. In addition, the salt useful in the present invention is of a concept including sodium chloride, calcium chloride, calcium carbonate, a mixture thereof and the like.

According to one embodiment of the present invention, the essential surfactant is used in an amount of 0.01 to 1 part by weight, preferably 0.01 to 0.8 part by weight, more preferably 0.01 to 0.6 part by weight, and still more preferably 0.01 to 0.5 part by weight, per 1 part by weight of the active ingredient. If the amount of the essential surfactant is too little as compared with the active ingredient, the grinding may not be performed well and there may be a problem in preventing the coagulation of the ground particles of the active ingredient. If the amount is too much, there may be a problem in molding the final drug products which are produced by using the prepared nanoparticle powder. If necessary, different types of auxiliary surfactants may be used additionally, and at this time the auxiliary surfactant may be added in an amount of 0 to 1 part by weight per 1 part by weight of the active ingredient.

According to one embodiment of the present invention, the biocompatible polymer may be used in an amount of, for example, 0.01 to 5 parts by weight, preferably 0.01 to 2 parts by weight, and more preferably 0.01 to 1 part by weight, per 1 part by weight of the active ingredient. If the amount of the biocompatible polymer is too less as compared with the active ingredient, the effects of using it cannot be obtained sufficiently. If the amount is too much, there may be problems in the form and drug compliance of the final drug products—which are produced by using the prepared nanoparticle powder.

According to one embodiment of the present invention, the saccharide or salt may be used in an amount of 0 to 5 parts by weight, preferably 0 to 4 parts by weight, more preferably 0 to 3 parts by weight, and still more preferably 0 to 2 parts by weight, per 1 part by weight of the active ingredient. If the amount of the saccharide or salt is too little as compared with the active ingredient, the effects of using it cannot be obtained sufficiently. If the amount is too much, there may be problems in the form and drug compliance of the final drug products—which are produced by using the prepared nanoparticle powder. The saccharide or salt may be added in powder form or in aqueous solution form. If added in aqueous solution form, it is preferable to make the water content in the resulting mixture 5% or less.

The mixture comprising an active ingredient, a surfactant having an HLB value of 8 or more and a melting point or a glass transition temperature of 80° C. or lower, optionally a biocompatible polymer, and optionally a saccharide or a salt as explained above preferably does not contain water. However, a small amount of water (for example, 5% by weight or less, based on the total weight of the mixture) may be added to perform the initial mixing and initial grinding well. Even if such a small amount of water is added, there is no problem in achieving the purpose of the present invention.

The mixture comprising an active ingredient, a surfactant having an HLB value of 8 or more and a melting point or a glass transition temperature of 80° C. or lower, optionally a biocompatible polymer, and optionally a saccharide or a salt as prepared above is subject to a continuous or repetitive grinding process using a roller mill (preferably, continuously grinding 20 or more times). In the grinding process, the ingredients constituting the mixture in a well-mixed state are lumped by compression and then ground by shearing force. In this case, the existence of saccharide or salt facilitates the repetitive grinding of the active ingredient, and consequently nanoparticles of the active ingredient can be prepared more efficiently.

The grinding process is performed generally at 90° C. or less, preferably at 60° C. or less, more preferably at 40° C. or less, and still more preferably at 30° C. or less. If the grinding process is performed at a low temperature, denaturation of the active ingredient by heat may be prevented, crystalline particles may maintain their crystallinity, and re-coagulation of the prepared particles may also be prevented effectively.

Effects of the Invention

According to the present invention, the limitation of difficulty in preparing particles having a size smaller than micrometer-scale in the traditional dry grinding process can be overcome. In addition, the problem of particle growth and size-up during the water-removal step after the grinding step due to the use of a lot of water in the traditional wet grinding process can be solved. Furthermore, nanoparticles can be prepared easily and effectively even in the case of active ingredients having relatively low water solubility.

MODE FOR CARRYING OUT THE INVENTION

The present invention is explained in detail through the following examples. However, the scope of the present invention is not limited thereto.

Examples 1 to 9

To 1 part by weight of itraconazole as a model drug, 0.5 part by weight of Gelucire® 50/13 (stearoyl polyoxyl-32 glycerides, melting point: 50° C., HLB: 13), which is a nonionic PEG-ester surfactant, as an essential surfactant, 0.5 part by weight of polyvinylpyrrolidone (PVP) k30 as a biocompatible polymer, and 2 parts by weight of mannitol as a saccharide were uniformly mixed. In order to know the influence of the water content in the mixture on the resulting particle size, deionized water in an amount corresponding to 1 or 5% by weight of the total mixture powder was added to the mixtures of some examples, and then uniformly mixed again. For the prepared mixtures, a grinding process was performed continuously 30 times by using a roller mill with a roller temperature set to 20, 30 or 40° C. according to the examples, to prepare powder of the particles containing the active ingredient. The prepared powder was added to deionized water with a concentration of 1 mg/ml based on itraconazole, stirred for 25 minutes, and then treated with sonication for 1 minute for complete dispersion, and the particle sizes were measured with HORIBA-LA950. The roller temperature, added water content and measured particle size (Mean Size: average particle size; Median Size: particle size at the median value (50%) of the particle size distribution) for each of the examples are shown in the following Table 1.

TABLE 1

| Example | Roller temperature (° C.) | Added water content (%) | Mean Size (μm) | Median Size (μm) |
|---|---|---|---|---|
| 1 | 20 | 0 | 0.739 | 0.310 |
| 2 | 20 | 1 | 0.712 | 0.331 |
| 3 | 20 | 5 | 0.887 | 0.339 |
| 4 | 30 | 0 | 0.459 | 0.305 |
| 5 | 30 | 1 | 0.428 | 0.337 |
| 6 | 30 | 5 | 0.465 | 0.299 |
| 7 | 40 | 0 | 0.398 | 0.308 |
| 8 | 40 | 1 | 0.419 | 0.327 |
| 9 | 40 | 5 | 0.409 | 0.309 |

From the results of Table 1, it can be known that the median size was nearly constant regardless of the temperature and water content. As for the mean size, it showed a considerable difference from the median size at the roller temperature of 20° C., and the difference was reduced at the roller temperatures of 30° C. and 40° C. However, after changing the time of sonication treatment to 3 minutes, the results of measuring the particle size showed that the mean size was similar to the median size throughout the whole area of the experimental temperature. This means that the grinding of the powder prepared at the roller temperature of 20° C. was not insufficient but its dispersion in water was slower as compared with the powder prepared at the roller temperatures of 30° C. and 40° C. That is, it was confirmed that at the roller mill condition (i.e., the roller temperature) of 40° C. or lower, uniformly ground nanoparticles were prepared.

Example 10

Nanoparticles containing itraconazole were prepared by the same method as in Example 1, except that mannitol was not used. The particle size thereof was measured by the same method as in Example 1. The measured mean size was 0.434 μm, and the median size was 0.379 μm.

Examples 11 to 14

1 part by weight of itraconazole and 1 part by weight of Gelucire® 50/13 as an essential surfactant were uniformly mixed. Deionized water in an amount corresponding to 1 or 5% by weight of the total mixture powder was added to the mixtures of some examples and then uniformly mixed again. For the prepared mixtures, a grinding process was performed continuously 30 times by using a roller mill with a roller temperature set to 20° C. or 40° C. according to the examples, to prepare powder of the particles containing the active ingredient. The prepared powder was added to deionized water with a concentration of 1 mg/ml based on itraconazole, stirred for 25 minutes, and then treated with sonication for 1 minute for complete dispersion, and the particle sizes were measured with HORIBA-LA950. The roller temperature, added water content and measured particle size (Mean Size, Median Size) for each of the examples are shown in the following Table 2.

TABLE 2

| Example | Roller temperature (° C.) | Added water content (%) | Mean Size (μm) | Median Size (μm) |
|---|---|---|---|---|
| 11 | 20 | 0 | 0.540 | 0.368 |
| 12 | 20 | 1 | 0.802 | 0.382 |
| 13 | 20 | 5 | 1.235 | 0.362 |
| 14 | 40 | 5 | 2.387 | 0.423 |

Example 15

1 part by weight of itraconazole, 1 part by weight of polyoxyethylene stearate (melting point: 37.2° C., HLB: 16.9) as an essential surfactant, and 2 parts by weight of mannitol were uniformly mixed. For the prepared mixture, a grinding process was performed continuously 30 times by using a roller mill with a roller temperature set to 25° C. to prepare powder of the particles containing the active ingredient. The prepared powder was added to deionized water with a concentration of 1 mg/ml based on itraconazole, stirred for 25 minutes, and then treated with sonication for 1 minute for complete dispersion, and the particle sizes were measured with HORIBA-LA950. The measured mean size was 0.378 μm, and the median size was 0.327 μm.

Example 16

2 g of coenzyme $Q_{10}$ as an active ingredient, 1.8 g of sucrose fatty acid ester (melting point: 55° C., HLB: 16) as an essential surfactant, 0.2 g of SLS (sodium lauryl sulfate) as an auxiliary surfactant, and 6 g of sucrose as a saccharide were mixed sufficiently by using a home mixer at room temperature. For the prepared mixture, a grinding process was performed 20 times by using a roll mill at room temperature to yield 9.2 g of powder of the particles containing coenzyme $Q_{10}$. The prepared powder was added to deionized water with a concentration of 1 mg/ml based on coenzyme $Q_{10}$, and stirred for 30 minutes at room temperature. The particle sizes were analyzed with HORIBA-LA950 to give the following results (unit: μm).

| D10 | D50 (= Median Size) | D90 | Mean Size |
|---|---|---|---|
| 0.226 | 0.319 | 0.4473 | 0.330 |

Example 17

5 g of talniflunate as an active ingredient, 1 g of polyoxyethylene stearate (melting point: 37.2° C., HLB: 16.9) as an essential surfactant, 1.5 g of poloxamer (188) as a biocompatible polymer, 9 g of lactose as a saccharide, and 0.5 ml of deionized water were mixed uniformly by using a home mixer. For the prepared mixture, a grinding process was performed 30 times by using a roll mill at room temperature to yield 15 g of powder of the particles containing talniflunate. The prepared powder was stirred for 10 minutes at room temperature and then treated with sonication for 3 minutes. The particle sizes were analyzed with HORIBA-LA950 to give the following results (unit: μm).

| D10 | D50 (= Median Size) | D90 | Mean Size |
|---|---|---|---|
| 0.0584 | 0.2851 | 0.3311 | 0.2584 |

Comparative Examples 1 to 4

1 part by weight of itraconazole and 1 part by weight of polyvinylpyrrolidone (PVP) k30 as a biocompatible polymer, together with 2 parts by weight of mannitol in Comparative Example 1, were mixed and the particles containing the active ingredient were prepared by the same method as in Example 1. The particle size of the prepared particles was measured by the same method as in Example 1. The roller temperature, added water content, mannitol amount and measured particle size (Mean Size, Median Size) for each of the Comparative Examples are shown in the following Table 3.

TABLE 3

| Comparative Example | Roller temperature (° C.) | Added water content (%) | Mannitol Amount (part by weight) | Mean Size (μm) | Median Size (μm) |
|---|---|---|---|---|---|
| 1 | 20 | 0 | 2 | 6.013 | 0.363 |
| 2 | 20 | 0 | 0 | 11.685 | 0.577 |
| 3 | 40 | 0 | 0 | 59.373 | 50.729 |
| 4 | 40 | 5 | 0 | 49.82 | 40.023 |

As can be seen from Table 3 above, when the particles were prepared by only using a biocompatible polymer or a biocompatible polymer and a saccharide, without using the essential surfactant of the present invention, a large amount of particles remained unground.

Comparative Example 5

1 part by weight of itraconazole and 2 parts by weight of mannitol were uniformly mixed and then 5% (w/w) of deionized water based on the total mixture was added thereto and uniformly mixed again. For the mixture, a grinding process was performed continuously 30 times under the roller condition of 40° C. to prepare powder of the particles containing the active ingredient. The prepared powder was added to deionized water with a concentration of 1 mg/ml based on itraconazole, stirred for 25 minutes, and then treated with sonication for 1 minute for complete dispersion, and the particle sizes were measured with HORIBA-LA950. The measured mean size was 165.785 μm, and the median size was 70.856 μm, by which it was confirmed that grinding to nanoscale particles was not achieved.

Comparative Example 6

1 part by weight of itraconazole and 1 part by weight of SLS (sodium lauryl sulfate, melting point: 206° C.) as a surfactant were uniformly mixed. For the mixture, a grinding process was performed continuously 30 times under the roller condition of 20° C. to prepare powder of the particles containing the active ingredient. The prepared powder was added to deionized water with a concentration of 1 mg/ml based on itraconazole, stirred for 25 minutes, and then treated with sonication for 1 minute for complete dispersion, and the particle sizes were measured with HORIBA-LA950. The measured mean size was 2.388 μm, and the median size was 0.459 μm, by which it was confirmed that unground large particles were present considerably.

Comparative Example 7

1 part by weight of itraconazole, 1 part by weight of SLS and 2 parts by weight of mannitol were uniformly mixed. The mixture was ground by the same method under the same condition as in Example 15, and the particle size was measured by the same method. The measured mean size was 2.699 μm, and the median size was 0.345 μm, by which it was confirmed that unground large particles were present considerably.

Comparative Example 8

Particles containing itraconazole were prepared by the same method as in Example 4, except that SLS was used instead of Gelucire® 50/13. The measured mean size was 13.859 μm, and the median size was 4.716 μm, by which it was confirmed that the particle size was generally bigger as compared with Example 4 and unground large particles were present considerably.

The invention claimed is:
1. A method for preparing nanoparticle powder of an active ingredient, comprising:
    (1) uniformly mixing an active ingredient with a surfactant having an HLB value of 8 or more and a melting point or a glass transition temperature of 80° C. or lower; and
    (2) grinding the mixture obtained in step (1) by using a roller mill,
    wherein water is added to the mixture in step (1) or step (2) and the amount of water is 1% to 5% by weight, based on the total weight of the mixture obtained in step (1).
2. The method for preparing nanoparticle powder of an active ingredient according to claim 1, wherein the mixture obtained in step (1) further comprises a biocompatible polymer.
3. The method according to claim 2, wherein the biocompatible polymer is selected from the group consisting of gelatin, casein, dextran, gum arabic, tragacanth, polyethyleneglycols, carboxymethylcellulose, hydroxypropylcellulose, hydroxypropylmethylcellulose, methylcellulose, hydroxyethylcellulose, hydroxypropylmethylcellulose phthalate, noncrystalline cellulose, polyvinylalcohol, polyvinylpyrrolidone, poloxamers, eudragit, lysozyme, albumin and mixtures thereof.

4. The method according to claim 2, wherein the active ingredient is one or more selected from the group consisting of physiologically active organic compounds, organometallic compounds, natural extracts, peptides, proteins and polysaccharides, and wherein the surfactant is selected from the group consisting of phospholipids, benzalkonium chloride, glycerin esters of fatty acid, cetomacrogol, polyoxyethylene alkyl ethers, polyoxyethylene stearate, polyoxyethylene fatty acid esters, sorbitan esters, polyoxyethylene castor oil derivatives, polyoxyethylene sorbitan fatty acid esters, sucrose fatty acid esters, PEG-cholesterol, PEG-vitamin E and mixtures thereof, and wherein the biocompatible polymer is selected from the group consisting of gelatin, casein, dextran, gum arabic, tragacanth, polyethyleneglycols, carboxymethylcellulose, hydroxypropylcellulose, hydroxypropylmethylcellulose, methylcellulose, hydroxyethylcellulose, hydroxypropylmethylcellulose phthalate, noncrystalline cellulose, polyvinylalcohol, polyvinylpyrrolidone, poloxamers, eudragit, lysozyme, albumin and mixtures thereof.

5. The method according to claim 1, wherein the mixture obtained in step (1) further comprises a saccharide or a salt.

6. The method according to claim 5, wherein the saccharide is glucose, lactose, mannitol, sucrose, xylitol, chitosan, starch, fiber or a mixture thereof.

7. The method according to claim 5, wherein the salt is sodium chloride, calcium chloride or calcium carbonate, or a mixture thereof.

8. The method according to claim 5, wherein the active ingredient is one or more selected from the group consisting of physiologically active organic compounds, organometallic compounds, natural extracts, peptides, proteins and polysaccharides, and wherein the surfactant is selected from the group consisting of phospholipids, benzalkonium chloride, glycerin esters of fatty acid, cetomacrogol, polyoxyethylene alkyl ethers, polyoxyethylene stearate, polyoxyethylene fatty acid esters, sorbitan esters, polyoxyethylene castor oil derivatives, polyoxyethylene sorbitan fatty acid esters, sucrose fatty acid esters, PEG-cholesterol, PEG-vitamin E and mixtures thereof, and wherein the saccharide is glucose, lactose, mannitol, sucrose, xylitol, chitosan, starch, fiber or a mixture thereof.

9. The method according to claim 5, wherein the active ingredient is one or more selected from the group consisting of physiologically active organic compounds, organometallic compounds, natural extracts, peptides, proteins and polysaccharides, and wherein the surfactant is selected from the group consisting of phospholipids, benzalkonium chloride, glycerin esters of fatty acid, cetomacrogol, polyoxyethylene alkyl ethers, polyoxyethylene stearate, polyoxyethylene fatty acid esters, sorbitan esters, polyoxyethylene castor oil derivatives, polyoxyethylene sorbitan fatty acid esters, sucrose fatty acid esters, PEG-cholesterol, PEG-vitamin E and mixtures thereof, and wherein the salt is sodium chloride, calcium chloride or calcium carbonate, or a mixtures thereof.

10. The method according to claim 1, wherein the active ingredient is one or more selected from the group consisting of physiologically active organic compounds, organometallic compounds, natural extracts, peptides, proteins and polysaccharides.

11. The method according to claim 1, wherein the surfactant is selected from the group consisting of phospholipids, benzalkonium chloride, glycerin esters of fatty acid, cetomacrogol, polyoxyethylene alkyl ethers, polyoxyethylene stearate, polyoxyethylene fatty acid esters, sorbitan esters, polyoxyethylene castor oil derivatives, polyoxyethylene sorbitan fatty acid esters, sucrose fatty acid esters, PEG-cholesterol, PEG-vitamin E and mixtures thereof.

12. The method according to claim 1, wherein the grinding in step (2) is performed continuously 20 or more times.

13. The method according to claim 1, wherein the temperature of the roller of the roller mill is 40° C. or lower.

14. The method according to claim 1, wherein the active ingredient is one or more selected from the group consisting of physiologically active organic compounds, organometallic compounds, natural extracts, peptides, proteins and polysaccharides, and wherein the surfactant is selected from the group consisting of phospholipids, benzalkonium chloride, glycerin esters of fatty acid, cetomacrogol, polyoxyethylene alkyl ethers, polyoxyethylene stearate, polyoxyethylene fatty acid esters, sorbitan esters, polyoxyethylene castor oil derivatives, polyoxyethylene sorbitan fatty acid esters, sucrose fatty acid esters, PEG-cholesterol, PEG-vitamin E and mixtures thereof.

* * * * *